United States Patent
Brackhagen et al.

(10) Patent No.: US 10,450,424 B2
(45) Date of Patent: *Oct. 22, 2019

(54) PROCESS FOR PRODUCING DISPERSION OF ESTERIFIED CELLULOSE ETHER

(71) Applicant: Dow Global Technologies LLC, Midland, MI (US)

(72) Inventors: Meinolf Brackhagen, Walsrode (DE); Neal J. Fetner, Midland, MI (US); Matthias Knarr, Nienburg/Weser (DE); Jin Zhao, Midland, MI (US)

(73) Assignee: DOW GLOBAL TECHNOLOGIES LLC

( * ) Notice: Subject to any disclaimer, the term of this patent is extended or adjusted under 35 U.S.C. 154(b) by 0 days.

This patent is subject to a terminal disclaimer.

(21) Appl. No.: 15/746,207

(22) PCT Filed: Jul. 8, 2016

(86) PCT No.: PCT/US2016/041455
§ 371 (c)(1),
(2) Date: Jan. 19, 2018

(87) PCT Pub. No.: WO2017/019276
PCT Pub. Date: Feb. 2, 2017

(65) Prior Publication Data
US 2018/0215880 A1    Aug. 2, 2018

Related U.S. Application Data

(60) Provisional application No. 62/197,605, filed on Jul. 28, 2015.

(51) Int. Cl.
A61K 47/38 (2006.01)
C08J 3/07 (2006.01)
(Continued)

(52) U.S. Cl.
CPC .................. C08J 3/07 (2013.01); A61K 9/10 (2013.01); A61K 47/38 (2013.01); C08B 13/00 (2013.01);
(Continued)

(58) Field of Classification Search
None
See application file for complete search history.

(56) References Cited

U.S. PATENT DOCUMENTS 4,226,981 A    10/1980  Onda et al.
4,341,563 A     7/1982  Kurihara et al.
(Continued)

FOREIGN PATENT DOCUMENTS

EP    0648487    4/1995
EP    0662323    7/1995
(Continued)

*Primary Examiner* — Melvin C. Mayes
*Assistant Examiner* — Colette B Nguyen

(57) ABSTRACT

A process for producing an aqueous composition comprising a dispersed esterified cellulose ether comprises the steps of grinding, in the presence of an aqueous diluent an esterified cellulose ether comprising (i) groups of the formula —C(O)—R—COOA or (ii) a combination of aliphatic monovalent acyl groups and groups of the formula —C(O)—R—COOA, wherein R is a N divalent aliphatic or aromatic hydrocarbon group and A is hydrogen or a cation, blending a salt of a fatty acid with the esterified cellulose ether and choosing the amounts of aqueous diluent, esterified cellulose ether and salt of a fatty acid that the produced aqueous composition comprises at least 20 percent of the dispersed esterified cellulose ether and heating the aqueous composition to a temperature of from 37 to 80 C during or after the grinding step.

13 Claims, 2 Drawing Sheets

(51) Int. Cl.
*C08B 13/00* (2006.01)
*C09D 101/32* (2006.01)
*C08L 1/32* (2006.01)
*A61K 9/10* (2006.01)
*C08J 3/12* (2006.01)

(52) U.S. Cl.
CPC . *C08J 3/12* (2013.01); *C08L 1/32* (2013.01); *C09D 101/32* (2013.01); *C08J 2301/32* (2013.01)

(56) References Cited

U.S. PATENT DOCUMENTS

| | | | |
|---|---|---|---|
| 4,365,060 A | | 12/1982 | Onda et al. |
| 4,540,566 A | * | 9/1985 | Davis ............... A61K 9/2013 424/480 |
| 7,138,143 B1 | | 11/2006 | Mukai et al. |
| 9,040,033 B2 | * | 5/2015 | Miller ............... A61K 9/146 424/78.31 |
| 2017/0173159 A1 | * | 6/2017 | Fetner ............... A61K 47/38 |
| 2017/0181977 A1 | * | 6/2017 | Zhao ............... B29C 41/14 |
| 2018/0215880 A1 | * | 8/2018 | Brackhagen ........... A61K 47/38 |
| 2018/0282526 A1 | * | 10/2018 | Petermann ............. B29C 41/14 |

FOREIGN PATENT DOCUMENTS

| | | |
|---|---|---|
| EP | 0677322 | 10/1995 |
| EP | 2810660 | 12/2014 |
| JP | 7070203 | 3/1995 |
| JP | 8109124 | 4/1996 |
| WO | 2008122993 | 10/2008 |
| WO | 2013164122 | 11/2013 |

* cited by examiner

PROCESS FOR PRODUCING DISPERSION OF ESTERIFIED CELLULOSE ETHER

FIELD

This invention concerns a process for producing an aqueous composition comprising a dispersed esterified cellulose ether and a process for increasing the storage stability of an aqueous composition comprising a dispersed esterified cellulose ether.

INTRODUCTION

Esters of cellulose ethers, their uses and processes for preparing them are generally known in the art. Known methods of producing cellulose ether-esters include the reaction of a cellulose ether with an aliphatic monocarboxylic acid anhydride or a dicarboxylic acid anhydride or a combination thereof, for example as described in U.S. Pat. Nos. 4,226,981 and 4,365,060.

Various known esterified cellulose ethers are useful as enteric polymers for pharmaceutical dosage forms, such as methylcellulose phthalate (MCP), hydroxypropyl methylcellulose phthalate (HPMCP), methylcellulose succinate (MCS), or hydroxypropyl methylcellulose acetate succinate (HPMCAS). The esterified cellulose ethers are used for coating dosage forms, such as tablets, microparticulates or capsules. Enteric polymers protect the drug from inactivation or degradation in the acidic environment or prevent irritation of the stomach by the drug, but are dissolved in the intestinal canals to release the drug contained therein. U.S. Pat. No. 4,365,060 discloses enterosoluble capsules which are said to have excellent enterosolubility behavior.

Enteric coatings or capsules can be prepared from organic or aqueous solutions of esterified cellulose ethers. European Patent Applications EP 0 662 323 and EP 0 677 322 disclose methods of preparing an aqueous emulsion for coating solid pharmaceutical preparations wherein a cellulosic polymer is dissolved in an organic solvent miscible with water or in a mixture of the organic solvent with water to give a polymer solution having a polymer concentration of not more than 10 wt. %, the solution is mixed with (additional) water to disperse the solution in water, and then organic solvent is removed. The published Japanese Patent Application JP8109124-A discloses the production of coating powders from such emulsions by adding an anionic surfactant and spray-drying. However, organic solvents are often not desirable for pharmaceutical or nutritional uses. On the other hand, esterified cellulose ethers only have a limited solubility in water.

The published Japanese Patent Application JP7070203A discloses a process wherein a hydroxycarboxylic acid type cellulose derivative is spread in water and pulverised by a pulveriser having a specific design to produce a cellulose derivative having a mean particle size below 7 microns, especially below 5 microns.

European Patent Application EP 0 648 487 discloses an aqueous dispersion comprising 5 to 15 wt. % of an enteric coating base, such as HPMCAS or HPMCP. The aqueous dispersion further comprises 15-40 wt. % of a plasticizer, such as triethyl citrate or triacetin, and 0.1-10 wt. % of an anionic surfactant, such as sodium alkyl sulfate, or a sodium or potassium salt of a fatty acid, such as sodium oleate or potassium sorbate, based on the weight of HPMCAS or HPMCP.

International Patent Application WO 2013/164122 discloses an aqueous composition for the manufacture of capsule shells comprising 5-50 wt. % of a wide range of functional polymers. In the majority of the examples the capsules are produced from an Aquacoat CPD 30 dispersion, which is a 30 wt. % aqueous dispersion comprising 23 wt. % non-salified cellulose acetate phthalate (CAP) and 7 wt. % Poloxamer, optionally blended with a minor amount of a HPMCAS slurry. Often uniform films can be obtained. A HPMCAS dispersion comprising 14% solids is also disclosed. Although 20% triethyl citrate is used as a film forming aid, when pins are heated to 50° C. and dipped into the dispersion, the HPMCAS polymer aggregates but the film rapidly collapses and flows down.

It would be desirable to provide an aqueous dispersion which comprises more than the 15 or 14 wt. % of HPMCAS or HPMCP as disclosed in EP-A-0 648 487 and in WO 2013/164122. A high concentration of HPMCAS or HPMCP would be desirable to increase the efficiency of preparing films and capsules. An increased concentration of HPMCAS or HPMCP would reduce the amount of liquid diluent that needs to be removed, e.g. by evaporation, when preparing films and capsules. Unfortunately, an increased content of HPMCAS solids in the aqueous dispersion has the disadvantage of an increased viscosity at room temperature, i.e. at 20° C. However, a sufficiently low viscosity at about 20° C. is highly desirable. The dispersion should have a reasonably good flowability at 20° C. to facilitate its handling. Cooling the dispersion below 20° C. adds complexity and increases energy costs and is therefore not desirable.

HPMCAS particles generally become tacky and tend to agglomeration in aqueous dispersions at elevated temperatures. Finally the HPMCAS particles start to gel and the viscosity of the aqueous HPMCAS dispersion starts to significantly increase. The temperature at which the HPMCAS particles start to gel in the aqueous dispersion is designated hereafter as "phase transition temperature" of the dispersion.

Tackiness and agglomeration of HPMCAS particles and a low phase transition temperature of the dispersion, e.g., at 21° C. or less, is undesirable when the HPMCAS particles are subjected to high shear, e.g. when HPMCAS particles are to be mixed with other materials during preparation of HPMCAS dispersions or when the esterified cellulose ether particles are subjected to grinding in the presence of water to produce the aqueous dispersion. A phase transition temperature at 21° C. or less and excessively tacky esterified cellulose ether dispersions at high shear can lead to operational failures during production, such as plugging of the milling or mixing apparatus used for producing the esterified cellulose ether dispersions.

Whether a viscosity increase of an aqueous dispersion comprising HPMCAS particles is desirable when the aqueous dispersion is subjected to low shear depends to a large degree on the end-use of the aqueous dispersion, When the aqueous dispersion is gently agitated for forming capsule shells on dipping pins, a viscosity increase at elevated temperature is desired. The viscosity increase of the aqueous dispersion improves adherence of the aqueous dispersion to dipping pins. On the other hand, when the aqueous dispersion is used for coating substrates, such as tablets or capsules, good spray-ability of the aqueous dispersion is more important and a viscosity increase at elevated temperature is less desired.

Another important property of an aqueous composition comprising dispersed esterified cellulose ether particles is its storage stability. The size of the dispersed esterified cellulose ether particles preferably remain about the same over an extended time period, such as several weeks. When an aqueous dispersion of an esterified cellulose ether loses its storage stability, it solidifies accompanied by water exudation; then the dispersion loses its ability to flow under its own weight. It is preferred that an aqueous dispersion of an esterified cellulose ether can be stored for weeks or months while still maintaining its ability to flow under its own weight.

Fulfilling this wide variety of requirements is challenging. Much research effort has been spent on improving the known aqueous composition comprising dispersed esterified cellulose ethers.

One object of the present invention is to provide an aqueous composition comprising dispersed particles of an esterified cellulose ether which has a sufficiently low viscosity at a temperature of 20° C. to enable reasonably good flowability of the aqueous composition, even when the aqueous composition comprises at least 20 wt. % esterified cellulose ether. It is a preferred object of the present invention to provide an aqueous composition comprising dispersed esterified cellulose ethers particles which has a sufficiently low viscosity at a temperature of 20° C., even when the aqueous composition comprises at least 25 wt. % or even at least 30 wt. %, or in preferred embodiments even at least 35 wt. % esterified cellulose ether particles.

It is another object of the present invention to provide an aqueous dispersion comprising esterified cellulose ether particles which has good storage stability.

SUMMARY

One aspect of the present invention is a process for producing an aqueous composition comprising a dispersed esterified cellulose ether comprising the steps of grinding, in the presence of an aqueous diluent, at least one esterified cellulose ether comprising (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation, blending at least one salt of a fatty acid and optionally one or more adjuvants with the esterified cellulose ether before, during or after the grinding of the esterified cellulose ether and choosing the amounts of aqueous diluent, esterified cellulose ether, salt of a fatty acid, and optionally one or more adjuvants that the produced aqueous composition comprises at least 20 percent of the dispersed esterified cellulose ether, based on the total weight of the aqueous composition, and heating the aqueous composition to a temperature of from 37 to 80° C. during or after the grinding step.

Another aspect of the present invention is a process for increasing the storage stability of an aqueous composition comprising a) at least one dispersed esterified cellulose ether comprising (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation, and b) at least one salt of a fatty acid, wherein the aqueous composition having a temperature of less than 28° C. is provided and the composition is heated to a temperature of from 37 to 80° C.

DESCRIPTION OF EMBODIMENTS

Figure 1:
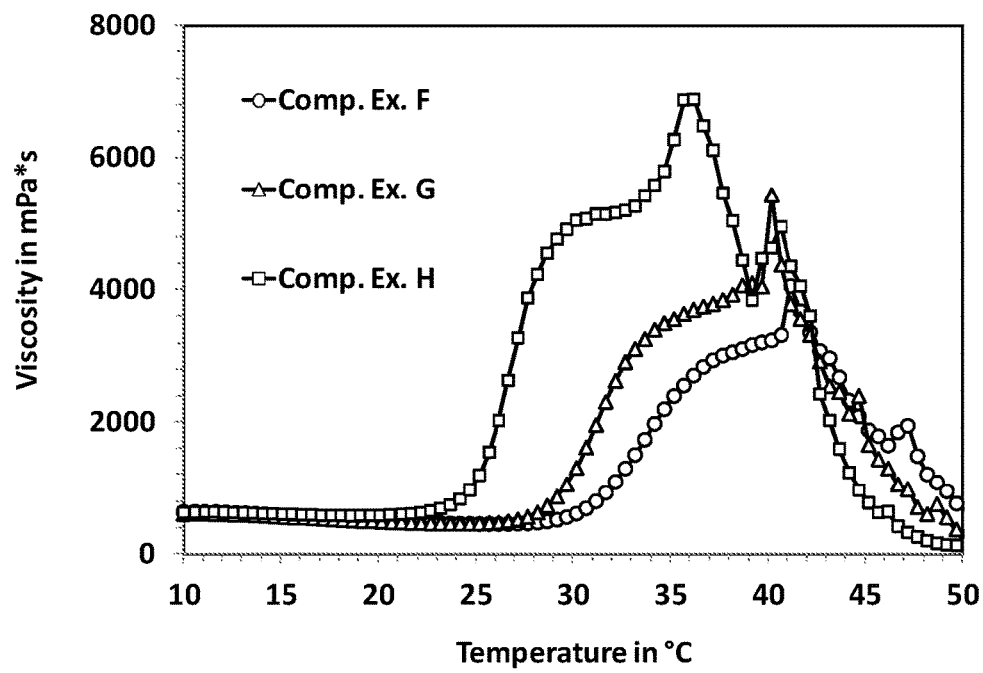
FIG. 1 illustrates the apparent viscosity of an aqueous dispersion of esterified cellulose ether particles produced according to a comparative process. The viscosities as a function of temperature were measured at different time periods of storing the produced aqueous dispersion.

Surprisingly, a process for producing an aqueous composition has been found wherein the composition comprises at least 20 wt. %, preferably at least 25 wt. %, more preferably at least 30 wt. %, and in the most preferred embodiments even at least 35 wt. % of dispersed particles of an esterified cellulose ether as described below, the composition has a reasonably low viscosity at a temperature of 20° C., and the composition has a good storage stability.

The esterified cellulose ether used in the process of the present invention has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether generally has a molar substitution of hydroxyalkoxyl groups of at least 0.05, preferably at least 0.08, more preferably at least 0.12, and most preferably at least 0.15. The degree of molar substitution is generally not more than 1.00, preferably not more than 0.90, more preferably not more than 0.70, and most preferably not more than 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers preferably have a DS(alkoxyl) of at least 1.0, more preferably at least 1.1, even more preferably at least 1.2, most preferably at least 1.4, and particularly at least 1.6. The DS(alkoxyl) is preferably not more than 2.5, more preferably not more than 2.4, even more preferably not more than 2.2, and most preferably not more than 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether utilized in the present invention has (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation. The cation preferably is an ammonium cation, such as $NH_4^+$ or an alkali metal ion, such as the sodium or potassium ion, more preferably the sodium ion. Most preferably, A is hydrogen.

The aliphatic monovalent acyl groups are preferably selected from the group consisting of acetyl, propionyl, and butyryl, such as n-butyryl or i-butyryl.

Preferred groups of the formula —C(O)—R—COOA are —C(O)—CH$_2$—CH$_2$—COOA, such as —C(O)—CH$_2$—CH$_2$—COOH or —C(O)—CH$_2$—CH$_2$—COO$^-$Na$^+$, —C(O)—CH=CH—COOA, such as —C(O)—CH=CH—COOH or —C(O)—CH=CH—COO$^-$Na$^+$, or —C(O)—C$_6$H$_4$—COOA, such as —C(O)—C$_6$H$_4$—COOH or —C(O)—C$_6$H$_4$—COO$^-$Na$^+$.

In the groups of formula —C(O)—C$_6$H$_4$—COOA the carbonyl group and the carboxylic group are preferably arranged in ortho-positions.

Preferred esterified cellulose ethers are
i) HPMCXY, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), or hydroxypropyl methylcellulose acetate succinate (HPMCAS), or ii) hydroxypropyl methyl cellulose phthalate (HPMCP), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of not more than 1.75, preferably not more than 1.50, more preferably not more than 1.25, and most preferably not more than 1.00, or even not more than 0.65. The degree of substitution of aliphatic monovalent acyl groups can be zero, but preferably it is at least 0.05, more preferably at least 0.10, and most preferably at least 0.20.

The esterified cellulose ethers generally have a degree of substitution of groups of formula —C(O)—R—COOA, such as succinoyl, of at least 0.05, preferably at least 0.10. The degree of substitution of groups of formula —C(O)—R—COOA generally is up to 1.6, preferably up to 1.30, more preferably up to 1.00, and most preferably up to 0.70 or even up to 0.60.

The sum of i) the degree of substitution of aliphatic monovalent acyl groups and ii) the degree of substitution of groups of formula —C(O)—R—COOA is generally at least 0.05, preferably at least 0.10, more preferably at least 0.20, most preferably at least 0.30, and particularly at least 0.40. The mentioned sum is generally no more than 2.0, preferably no more than 1.4, more preferably no more than 1.15, most preferably no more than 1.10 and particularly no more than 1.00.

The content of the acetate and succinate ester groups is determined according to "Hypromellose Acetate Succinate", United States Pharmacopeia and National Formulary, NF 29, pp. 1548-1550. Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left( \% \text{ MeO} * \frac{M(OCH_3) - M(OH)}{M(OCH_3)} \right) -$$

-continued $$\left(\% \text{ HPO} * \frac{M(OCH_2CH(OH)CH_3) - M(OH)}{M(OCH_2CH(OH)CH_3)}\right) -$$

$$\left(\% \text{ Acetyl} * \frac{M(COCH_3) - M(H)}{M(COCH_3)}\right) -$$

$$\left(\% \text{ Succinoyl} * \frac{M(COC_2H_4COOH) - M(H)}{M(COC_2H_4COOH)}\right)$$

$$DS(\text{Me}) = \frac{\frac{\% \text{ MeO}}{M(OCH_3)}}{\frac{\% \text{ cellulose backbone}}{M(AGU)}} \quad MS(\text{HP}) = \frac{\frac{\% \text{ HPO}}{M(HPO)}}{\frac{\% \text{ cellulose backbone}}{M(AGU)}}$$

$$DS(\text{Acetyl}) = \frac{\frac{\% \text{ Acetyl}}{M(\text{Acetyl})}}{\frac{\% \text{ cellulose backbone}}{M(AGU)}}$$

$$DS(\text{Succinoyl}) = \frac{\frac{\% \text{ Succinoyl}}{M(\text{Succinoyl})}}{\frac{\% \text{ cellulose backbone}}{M(AGU)}}$$

$$M(\text{MeO}) = M(OCH_3) = 31.03 Da$$

$$M(\text{HPO}) = M(OCH_2CH(OH)CH_3) = 75.09 Da$$

$$M(\text{Acetyl}) = M(COCH_3) = 43.04 Da$$

$$M(\text{Succinoyl}) = M(COC_2H_4COOH) = 101.08 Da$$

$$M(AGU) = 162.14 Da$$

$$M(OH) = 17.008 Da$$

$$M(H) = 1.008 Da$$

By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O-alkylene-OH); such as hydroxypropoxyl (i.e., —O—$CH_2CH(CH_3)$—OH). The content of the aliphatic monovalent acyl group is reported based on the mass of —C(O)—$R_1$ wherein $R_1$ is a monovalent aliphatic group, such as acetyl —(C(O)—$CH_3$). The content of the group of formula —C(O)—R—COOH is reported based on the mass of this group, such as the mass of succinoyl groups (i.e., —C(O)—$CH_2$—$CH_2$—COOH).

The esterified cellulose ether utilized in the present invention generally has a viscosity of at least 1.2 mPa·s, preferably least 1.8 mPa·s, and more preferably least 2.4 mPa·s, and generally no more than 200 mPa·s, preferably no more than 100 mPa·s, more preferably no more than 50 mPa·s, and most preferably no more than 30 mPa·s, measured as a 2.0 weight percent solution of the esterified cellulose ether in 0.43 wt % aqueous NaOH at 20° C. according to "Hypromellose Acetate Succinate, United States Pharmacopia and National Formulary, NF 29, pp. 1548-1550".

The process of the present invention comprises the steps of grinding, in the presence of an aqueous diluent, at least one esterified cellulose ether described above and blending at least one salt of a fatty acid and optionally one or more adjuvants with the esterified cellulose ether before, during or after the grinding of the esterified cellulose ether. The amounts of aqueous diluent, esterified cellulose ether, salt of a fatty acid, and optionally one or more adjuvants are chosen that the produced aqueous composition comprises at least 20 percent of the dispersed esterified cellulose ether, based on the total weight of the aqueous composition. An important aspect of the process of the present invention is heating the aqueous composition to a temperature of from 37 to 80° C. during or after the grinding step.

Grinding of at least one esterified cellulose ether described above is conducted in an aqueous diluent. The aqueous diluent is water, optionally mixed with a minor amount of an organic solvent. The aqueous diluent preferably consists of 50-100 weight percent, more preferably 65-100 weight percent, and most preferably 75-100 weight percent of water and preferably 0-50 weight percent, more preferably 0-35 weight percent, and most preferably 0-25 weight percent of an organic solvent, based on the total weight of water and the organic solvent. Useful organic solvents are polar organic solvents having one or more heteroatoms, such as oxygen, nitrogen or halogen like chlorine. More preferred organic solvents are alcohols, for example multifunctional alcohols, such as glycerol, or preferably monofunctional alcohols, such as methanol, ethanol, isopropanol or n-propanol; ethers, such as tetrahydrofuran, ketones, such as acetone; methyl ethyl ketone, or methyl isobutyl ketone; acetates, such as ethyl acetate; halogenated hydrocarbons, such as methylene chloride; or nitriles, such as acetonitrile. Preferably only water is used as aqueous diluent.

At least one salt of a fatty acid is blended with the esterified cellulose ether before, during or after the grinding of the esterified cellulose ether. Preferred fatty acid salts are ammonium, alkali metal or alkaline earth metal salts. A preferred ammonium ion is $NH_4^+$. Preferred alkali metal ions are the sodium or potassium ions. A preferred alkaline earth metal ion is the calcium ion. The fatty acids can be saturated or unsaturated. Exemplary of saturated fatty acids are caprylic acid, capric acid, lauric acid, myristic acid, palmitic acid, stearic acid, arachidic acid, behenic acid, lignoceric acid and cerotic acid. The unsaturated fatty acids can be mono-, di- or triunsaturated fatty acids, mono-unsaturated and di-unsaturated fatty acids being preferred. Exemplary of mono-unsaturated fatty acids are myristoleic acid, palmitoleic acid, sapienic acid, oleic acid, elaidic acid and vaccenic acid. Exemplary of di-unsaturated fatty acids are linoleic acid and linoelaidic acid Ammonium, alkali metal and alkaline earth metal salts of stearic acid or oleic acid are most preferred, particularly those salts mentioned above.

The amounts of aqueous diluent, esterified cellulose ether, salt of a fatty acid, and optionally one or more adjuvants are chosen that the produced aqueous composition comprises at least 20 percent, preferably at least 25 percent, more preferably at least 30 percent, and most preferably even at least 35 percent of the esterified cellulose ether(s) in dispersed state in the produced aqueous composition. The amount of dispersed esterified cellulose ether generally is up to 40 percent or in some cases even up to 43 percent. These percentages are based on the total weight of the composition.

In the process of the present invention the total amount of the salt(s) of a fatty acid is generally chosen that it is at least 0.05 percent, preferably at least 0.1 percent, more preferably at least 0.5 percent, most preferably at least 1.0 percent, and particularly at least 2.0 percent, based on the total weight of the esterified cellulose ether(s). The total amount of the salt(s) of a fatty acid generally is up to 20 percent, preferably up to 15 percent, more preferably up to 10 percent, most preferably up to 7.0 percent, and particularly only up to 5.0 percent, based on the total weight of the esterified cellulose ether(s).

The amount of the aqueous diluent is typically at least 50 percent, more typically at least 55 percent, based on the total weight of the aqueous composition. The amount of the aqueous diluent is typically no more than 79 percent, more typically no more than 75 percent, based on the total weight of the aqueous composition.

In a preferred embodiment of the present invention additionally an anionic surfactant comprising a sulfate or sulfonate group is blended with the esterified cellulose ether before, during or after the grinding of the esterified cellulose ether. The amount of anionic surfactant comprising a sulfate or sulfonate group is generally chosen in an amount of at least 0.01 percent, preferably at least 0.02 percent, more preferably at least 0.05 percent, most preferably at least 0.1 percent, and particularly at least 0.2 percent, based on the total weight of the esterified cellulose ether(s). The total amount of the anionic surfactant(s) comprising a sulfate or sulfonate group generally is up to 10 percent, preferably is up to 7 percent, more preferably up to 5 percent, most preferably up to 3 percent, and particularly only up to 1.5 percent, based on the total weight of the esterified cellulose ether(s). Preferred are ammonium, alkali metal or alkaline earth metal salts of the anionic surfactant comprising a sulfate or sulfonate group. The anionic surfactant can have one or more, preferably one or two, sulfate or sulfonate groups. A preferred ammonium ion is $NH_4^+$. Preferred alkali metal ions are the sodium or potassium ions. A preferred alkaline earth metal ion is the calcium ion. Preferably the anionic surfactant comprises one or more, preferably one or two, alkyl, alkenyl, alkinyl or cycloalkyl groups. Preferably the alkyl, alkenyl, alkinyl or cycloalkyl groups each independently comprise from 4 to 12 carbon atoms, more preferably from 6 to 8 carbon atoms. The total number of carbon atoms in the alkyl, alkenyl, alkinyl or cycloalkyl group(s) in the surfactant is preferably 8 to 24, more preferably 12 to 16. These groups can be branched or linear. Preferred anionic surfactants comprising a sulfate or sulfonate group are alkyl sulfate salts, such as ammonium lauryl sulfate, potassium lauryl sulfate, sodium dodecyl sulfate (SDS) or sodium laureth sulfate (SLES); or alkyl benzene sulphonates, such as sodium dodecylbenzenesulfonate, or alkyldiphenyloxide disulfonate salts, such as sodium dodecyl diphenyl ether disulfonate. More preferred anionic surfactants comprising a sulfate or sulfonate group are dialkyl, dialkenyl, dialkinyl or dicycloalkyl sulfosuccinates. Most preferred is a dialkyl sulfosuccinate, particularly dioctyl sodium sulfosuccinate (IUPAC name sodium 1,4-bis (2-ethylhexoxy)-1,4-dioxobutane-2-sulfonate), dioctyl potassium sulfosuccinate, or dioctyl calcium sulfosuccinate.

The salt of a fatty acid, optionally the anionic surfactant comprising a sulfate or sulfonate group and additional optional adjuvants for forming a dispersion are preferably added before or during the grinding of the esterified cellulose ether in the aqueous diluent. A salt of a fatty acid, an optional anionic surfactant comprising a sulfate or sulfonate group and optional adjuvants can also be added after the grinding of the esterified cellulose ether, but generally at least 50 percent of the salt of a fatty acid that is used for preparing the aqueous composition of the present invention is added before or during the grinding of the esterified cellulose ether.

The above-mentioned components are subjected to grinding for a sufficient time period to produce the desired particle size of the esterified cellulose ether. An aqueous composition in the form of an aqueous dispersion of the esterified cellulose ether in the aqueous diluent is produced by the process of the present invention. The median particle size, d50, of the dispersed esterified cellulose ether particles is typically up to 7 micrometers, more typically up to 5 micrometers, and even more typically up to 4 micrometers. The median particle size, d50, of the dispersed esterified cellulose ether particles is typically 0.3 micrometers or more, more typically 1.0 micrometers or more, and most typically 1.5 micrometers or more. The particle size is measured by laser diffraction particle size analysis, e.g., using a Beckman Coulter laser diffraction particle size analyzer which is commercially available from Beckman Coulter, Calif. The median particle size d50 is the diameter where 50 volume percent of the particles have a smaller equivalent diameter and 50 volume percent have a larger equivalent diameter. Typically d90 is 1.0 micrometers or more, more typically 2.0 micrometers or more, and most typically 4.0 micrometers or more; and typically up to 12 micrometers, more typically up to 10 micrometers, and most typically up to 7 micrometers, d90 being the diameter where 90 volume percent of the particles have a smaller equivalent diameter and the other 10 volume percent have a larger equivalent diameter. The equivalent particle diameter d is the diameter of a sphere having the same volume as the volume of a given particle. The mean particle diameter is typically 0.5 micrometers or more, more typically 1.0 micrometers or more, and most typically 2.0 micrometers or more; and typically up to 8 micrometers, more typically up to 6 micrometers, and most typically even only up to 4 micrometers.

Any grinding device suitable for grinding esterified cellulose ethers in the presence of an aqueous diluent to a median particle size d50 as indicated further above can be used. Preferred grinding devices are wet grinding units such as media mills or bead mills. Grinding is generally conducted for a sufficient time period to achieve an above-mentioned median particle size, d50, of the dispersed esterified cellulose ether particles. The grinding period is typically from 60 to180 minutes.

It has surprisingly been found that improved storage stability of the aqueous composition is achieved when the aqueous composition is heated to a temperature of from 37° C. to 80° C. during or after the grinding step. Preferably the temperature is at least 40° C., more preferably at least 45° C. The preferred temperature is not more than 70° C., more preferably not more than 55° C.

In one embodiment of the invention heating is conducted during the grinding step. In this embodiment the temperature during the grinding step should be closely monitored. Typically some heat is generated during grinding due to the energy input of the grinding device. Grinding devices used in the state of the art have a cooling system to avoid a significant temperature increase during grinding. In the embodiment of the present invention the speed of the grinding device and/or the efficiency of a cooling system should be controlled and adjusted to achieve a temperature of from 37° C. to 80° C., preferably from 40° C. to 70° C., and more preferably from 45° C. to 55° C. during the grinding step. If needed, heating is applied by a separate heating system to achieve a temperature of from 37° C. to 80° C. Preferably the temperature of the aqueous composition is maintained in the above-mentioned range for at least 30 minutes, preferably for at least 120 minutes, and more preferably for at least 150 minutes. Typically the temperature of the aqueous composition is maintained in the above-mentioned range for up to 24 hours, preferably up to 12 hours, and more preferably up to 5 hours.

The apparent viscosity of the aqueous composition produced according to the process of the present invention is generally 50 mPa·s or more, typically 100 mPa·s or more, measured at 20° C. The apparent viscosity of the aqueous composition of the present invention is generally no more than 5000 mPa·s, typically no more than 4000 mPa·s, measured at 20° C.

Upon preparation of the aqueous composition optional ingredients can be incorporated into the composition, for example active ingredients, such as fertilizers, herbicides, pesticides, or biologically active ingredients, such as vitamins, herbals or mineral supplements or drugs; or adjuvants such as one or more coloring agents, pigments, opacifiers, flavor or taste improvers, antioxidants, or any combination thereof. Optional additives are preferably pharmaceutically acceptable. The amount of these optional ingredients is typically from 0 to 50 percent of the total weight of the ingredients of the aqueous composition excluding the aqueous diluent. Typically the amount is 1 percent or more, more typically 5 percent or more; and typically up to 40 percent, more typically up to 20 percent of the total weight of the ingredients of the aqueous composition excluding the aqueous diluent. Some of the optional ingredients can be incorporated into the composition during the grinding step, but shear or heat sensitive ingredients are preferably added only after grinding.

In another aspect of the present invention the storage stability of an above-mentioned aqueous composition can be increased by providing an above-mentioned aqueous composition that has a temperature of less than 28° C., typically from 15 to 25° C., and more typically from 18 to 23° C., and heating the composition to a temperature of from 37 to 80° C., preferably from 40° C. to 70° C., and more preferably from 45° C. to 55° C. An above-mentioned aqueous composition that has a temperature of less than 28° C. can be produced as described above, except that no heating to a temperature of from 37 to 80° C. needs to be conducted during the grinding step. If the heating of the aqueous composition is only conducted after grinding, heating should be conducted before the aging of the composition. Generally the aqueous composition should not be stored more than 8 weeks, preferably not more than 6 weeks, more preferably not more than 4 weeks, and most preferably not more than 2 weeks at room temperature before it is heated. In this aspect of the invention, agitation of the aqueous composition during the above-mentioned heat treatment, such as stirring is preferably avoided to prevent agglomeration of the dispersed particles of esterified cellulose ether.

An aqueous dispersion of an esterified cellulose ether that has been heated during or after grinding as described above can usually be stored more than 3 months, in the most preferred embodiments even more than 6 months, without losing its ability to flow under its own weight if it does not comprise a film forming aid.

The salt of a fatty acid as described above initially stabilizes the aqueous dispersion of an esterified cellulose ether, even without the heat treatment described above. At this state, the dispersion is of low viscosity and well suitable for coating applications, for example for coating dosage forms such as tablets or for preparing capsule shells. When an aqueous dispersion of an esterified cellulose ether ages which has not been subjected to heat treatment as described above, e.g. during shipping and storage of the composition, the viscosity rises over time and agglomeration is observed at elevated temperature.

Furthermore, when preparing coatings and capsule shells, often film forming aids are utilized. Film forming aids are often used for their plasticizing properties to avoid or at least reduce brittleness of coatings or capsule shells. However, it is known that addition of large amounts of a film forming aid reduces the agglomeration temperature of the aqueous dispersion and the temperature at which the viscosity of the aqueous dispersion increases to a large extent when the dispersion is slightly heated. Agglomeration close to room temperature results in blocking of the spraying devices used for spaying the aqueous dispersion onto substrates to be coated. This problem is typically solved in the coating industry by applying the film forming agent through a separate spray nozzle, but this separate spraying is cumbersome.

Surprisingly, it has been found that aqueous dispersions of an esterified cellulose ether that have been heated during or after grinding as described above do not only exhibit an improved storage stability but also have a lower viscosity at elevated temperature, even when the aqueous dispersion comprises a film forming agent. Agglomeration upon addition of a film forming aid to a dispersion that has been subjected to heat treatment according to the present invention is not observed.

In one embodiment of the present invention, at least one film forming aid is added to the aqueous composition that has been heated to a temperature of from 37 to 80° C. as described above. The term "film forming aid" comprises one or more plasticizers conventionally used in the manufacture of coatings or capsule shells, notably hard capsule shells, to ensure the formation of self-supported cohesive films and avoid capsule brittleness, and/or one or more viscosity enhancers at elevated temperature, i.e. natural as well as synthetic substances conventionally used to optimize aqueous compositions for coating purposes or the dip molding manufacture of hard capsule shells.

Film forming aids that display plasticizing properties include: phthalic esters, such as dimethyl-, diethyl-, and diisopropyl-phthalate; citric esters, such as triethyl-, tributyl-, acetyltriethyl- and acetyltributyl-citrate; phosphoric esters, such as triethyl-, tricresyl, and triphenyl-phosphate; alkyl lactate; glycol esters; glycerol and glycerol esters, such as glycerol triacetate also known as triacetine; sucrose esters; oils and fatty acid esters; butyl stearate; dibutyl sebacate; dibutyl tartrate; diisobutyl adipate, tributyrin; propylene glycol; and mixtures thereof.

In one embodiment, film forming aids are cellulose ethers, such as carboxy methylcellulose, hydroxypropyl cellulose, ethyl cellulose, methylcellulose, hydroxypropylmethylcellulose (HPMC), e.g. HPMC types 2910, 2906 and/or 2208 as defined in USP30-NF25; gelatin, pullulan, non enteric starch derivatives, such as hydroxypropyl starch; polyvinyl acetate derivatives (PVAP); sorbitan monoesters; sorbitan polyoxyethylene esters; fatty acid esters; glycerol polyethylene, glycol ricinoleate; macrogolglycerides; triethyl citrate (TEC); acetyl trialkyl citrate; glycerol triacetate (triacetine); talc; and mixtures thereof.

In one embodiment the resulting aqueous composition comprises at least 5 percent, more preferably at least 10 percent, even more preferably at least 13 percent, and most preferably at least 15 percent of one or more film forming aids, such as plasticizers, based on the weight of the dispersed esterified cellulose ether. The amount of said one or more film forming aids, such as plasticizers, is generally up to 30 percent, preferably up to 25 percent, even more preferably up to 22 percent, and most preferably up to 20 percent, based on the weight of the dispersed esterified cellulose ether.

Some embodiments of the invention will now be described in detail in the following Examples.

EXAMPLES

Unless otherwise mentioned, all parts and percentages are by weight. In the Examples the following test procedures are used.

Viscosity of Hydroxypropyl Methyl Cellulose Acetate Succinate (HPMCAS)

A 2.0% by weight solution of the HPMCAS in 0.43 wt. % aqueous NaOH was prepared as described in "Hypromellose Acetate Succinate, United States Pharmacopia and National Formulary, NF 29, pp. 1548-1550, followed by an Ubbelohde viscosity measurement at 20° C. according to DIN 51562-1:1999-01 (January 1999).

Content of Ether and Ester Groups of HPMCAS

The content of ether groups in HPMCAS was determined in the same manner as described for "Hypromellose", United States Pharmacopeia and National Formulary, USP 35, pp 3467-3469. The ester substitution with acetyl groups (—CO—$CH_3$) and the ester substitution with succinoyl groups (—CO—$CH_2$—$CH_2$—COOH) were determined according to Hypromellose Acetate Succinate, United States Pharmacopia and National Formulary, NF 29, pp. 1548-1550". Reported values for ester substitution were corrected for volatiles (determined as described in section "loss on drying" in the above HPMCAS monograph).

HPMCAS Particle Size Measurement in the Aqueous Dispersion

To measure particle sizes 1-2 g of the aqueous HPMCAS dispersion that had been produced as described below was diluted in 20 ml of purified water. The particle size in the diluted dispersion was measured by laser diffraction particle size analysis using a Beckman Coulter LS 13 320 laser diffraction particle size analyzer which is commercially available from Beckman Coulter, California. The Universal Liquid Module (ULM) with a Fraunhofer optical model, a Polarization Intensity Differential Scattering (PIDS) system and a sonication control snit, were used. In the sonication control unit the HPMCAS dispersion was subjected to ultrasonic treatment for a time period of up to 120 seconds during the HPMCAS addition (about 30 seconds) and particle size measurement (about 90 seconds).

Stability After About 2 Weeks

To assess the stability of the aqueous HPMCAS dispersion about 2 weeks after its preparation, the HPMCAS particle size measurement described above was repeated after about 2 weeks. The degree of changes in particle size was a clear indication of the stability of the aqueous HPMCAS dispersion. The dispersion was also visually inspected.

Apparent Viscosity of the Aqueous Dispersion Comprising HPMCAS

The apparent viscosity of the aqueous dispersion comprising HPMCAS was measured at various temperatures according to a temperature sweep experiment performed with a Anton Paar MCR 301 rheometer with a CC-27 cup geometry and a 4-blade vane geometry ST26-4V-20 over a temperature range of 10 to 50° C. with a heating rate of 0.5° C./min and a constant speed of the vane geometry of 40 rpm and a measurement point duration of 0.25 min. Prior to this temperature sweep testing the material was treated for 30 min at 10° C. at 250 rpm. A sample volume of 20 ml was used for these measurements. The samples had been stored at room temperature prior to the viscosity measurement.

Determination of Storage Stability by Visual Inspection ("Visual Storage Stability")

The HPMCAS dispersion was stored at ambient temperature over several weeks and evaluated by visual inspection. The dispersion was considered to be storage stable at a given point in time when the dispersion was still flowing under its own weight. The dispersion was considered to have lost its storage stability when it had solidified accompanied by water exudation; then the dispersion had lost its ability to flow under its own weight.

Determination of Storage Stability by Measuring the Apparent Viscosity of the Aqueous Dispersion Comprising HPMCAS The apparent viscosity of the aqueous dispersion comprising HPMCAS was measured at various temperatures according to a temperature sweep experiment as described further above at several time periods after production of the aqueous dispersion. The change in apparent viscosity as a function temperature of the aqueous composition over time is an indication of the storage stability of the aqueous dispersion.

Determination of Solids Content

The solids content was determined using a moisture balance (Mettler Toledo Advanced Moisture Analyzer, Model HB43-S). Instrument settings were as follows: 3 g dispersion using the Rapid drying program with a temperature set point of 120° C. (40% overshoot for first 3 minutes) with switch-off criteria 5 (less than 1 mg weight change over 140 seconds). Upon drying to remove water, the residual solids content (including all additives) was weighed.

HPMCAS Used for Preparing the Aqueous Dispersion in Comparative Examples A-E

HPMCAS was used that had 23.7% methoxyl groups ($DS_{methoxyl}$=1.93), 7.1% hydroxypropoxyl groups ($MS_{hydoxypropoxyl}$=0.24), 9.6% acetyl groups ($DS_{acetyl}$=0.56), 10.5% succinoyl groups ($DS_{succinoyl}$=0.26), and a viscosity of 2.96 mPa·s, measured as a 2.0% by weight solution of the HPMCAS in 0.43 wt. % aqueous NaOH.

HPMCAS Used in Comparative Examples F-H

HPMCAS was used that had 23.2% methoxyl groups ($DS_{methoxyl}$=1.91), 7.3% hydroxypropoxyl groups ($MS_{hydoxypropoxyl}$=0.25), 9.3% acetyl groups ($DS_{acetyl}$=0.55), 11.2% succinoyl groups ($DS_{succinoyl}$=0.28), and a viscosity of 2.91 mPa·s, measured as a 2.0% by weight solution of the HPMCAS in 0.43 wt. % aqueous NaOH.

HPMCAS Used in Comparative Examples I-K and in Examples 1 and 2, 9a-9h and 10a, 10b and 10c HPMCAS was used that had 23.2% methoxyl groups ($DS_{methoxyl}$=1.92), 7.3% hydroxypropoxyl groups ($MS_{hydoxypropoxyl}$=0.25), 9.7% acetyl groups ($DS_{acetyl}$=0.58), 11.1% succinoyl groups ($DS_{succinoyl}$=0.28), and a viscosity of 2.9 mPa·s, measured as a 2.0% by weight solution of the HPMCAS in 0.43 wt. % aqueous NaOH.

HPMCAS Used in Examples 3-5

HPMCAS was used that had 23.0% methoxyl groups ($DS_{methoxyl}$=1.89), 7.3% hydroxypropoxyl groups ($MS_{hydoxypropoxyl}$=0.25), 9.1% acetyl groups ($DS_{acetyl}$=0.54), 11.6% succinoyl groups ($DS_{succinoyl}$=0.29), and a viscosity of 2.9 mPa·s, measured as a 2.0% by weight solution of the HPMCAS in 0.43 wt. % aqueous NaOH.

HPMCAS Used for Preparing the Aqueous Dispersions in Examples 6 and 7

HPMCAS was used that had 23.2% methoxyl groups ($DS_{methoxyl}$=1,90), 7.4% hydroxypropoxyl groups ($MS_{hydoxypropoxyl}$=0.25), 9.4% acetyl groups ($DS_{acetyl}$=0.56), 11.0% succinoyl groups ($DS_{succinoyl}$=0.28), and a viscosity of 3.0 mPa·s, measured as a 2.0% by weight solution of the HPMCAS in 0.43 wt. % aqueous NaOH.

HPMCAS Used for Preparing the Aqueous Dispersions in Example 8

A mixture of the same HPMCAS as used in Examples 6 and 7 and another HPMCAS was used. The other HPMCAS had 23.0% methoxyl groups ($DS_{methoxyl}$=1.89), 7.3% hydroxypropoxyl groups ($MS_{hydroxypropoxyl}$=0.25), 9.8% acetyl groups ($DS_{acetyl}$=0.58), 10.8% succinoyl groups ($DS_{succinoyl}$=0.27), and a viscosity of 2.9 mPa·s, measured as a 2.0% by weight solution of the HPMCAS in 0.43 wt. % aqueous NaOH.

HPMCAS Used in Comparative Examples La and Lb

HPMCAS was used that had 23.0% methoxyl groups ($DS_{methoxyl}$=1.89), 7.3% hydroxypropoxyl groups ($MS_{hydoxypropoxyl}$=0.25), 9.1% acetyl groups ($DS_{acetyl}$=0.54), 11.6% succinoyl groups ($DS_{succinoyl}$=0.29), and a viscosity of 2.9 mPa·s, measured as a 2.0% by weight solution of the HPMCAS in 0.43 wt. % aqueous NaOH.

Comparative Examples A-E

To produce an aqueous HPMCAS dispersion, water was loaded first and recirculated through a Netzsch LAB STAR media mill (1.4 mm Ytterum Stabilized Zirconia media, 0.7 mm screen size). During the milling process HPMCAS solids and a surfactant as listed in Table 1 below were loaded gradually to water recirculating through the mill at a mill speed of 3600 rev/min. The HPMCAS and the surfactant were added at a predetermined weight ratio to provide a percentage of surfactant, based on HPMCAS, as listed in Table 1 below. Addition of HPMCAS and surfactant was continued until a total solids loading of 20-30% was achieved, based on the total weight of the composition. The percentage of HPMCAS, based on the total weight of the composition, was calculated from the measured solids content and the given weight ratio between HPMCAS and the surfactant. The results are listed in Table 1 below. Following the addition of all solids, milling continued until the final particle size was obtained. Comparative Examples A, B, D and E were completed using a similar procedure. In Comparative Example C no dispersion was obtained as the viscosity of the dispersion caused a pressure in the mill that exceeded the allowable pressure system.

In Comparative Example A no additive, i.e. no surfactant, was used. In Comparative Example B the well-known non-ionic surfactant polyoxyethylene (20) sorbitan monooleate, commercially available under the Trademark Tween 80 was used. In Comparative Examples C and D sodium dodecyl sulfate (SDS) was used, which is a well-known anionic surfactant. In Comparative Example E a block copolymer of ethylene oxide and propylene oxide, which is commercially available from BASF under the Trademark Pluronic L44 NF INH, was used as non-ionic surfactant.

The dispersion of Comparative Example B had HPMCAS particles that were very large. In Comparative Example C no dispersion was obtained as the viscosity of the dispersion caused a pressure in the mill that exceeded the allowable system pressure. The dispersions of Comparative Examples A, B and D produced a dispersion with acceptable viscosity and particle size but with tendency to agglomerate upon storage for about 2 weeks. The dispersion of Comparative Example E displayed an increased particle size after 2 weeks. The dispersions of Comparative Examples A-E were not suitable for reasonably convenient handling and processing.

Comparative Examples F-H

Comparative Examples A E were repeated except that sodium stearate as listed in Table 1 was used as a surfactant. Comparative Examples F H are similar to the Examples in co-pending International patent application PCT/US15/018390 having a filing date of 3 Mar. 2015 and a first priority date of 8 Apr. 2014.

14 days (Comparative Example F), 27 days (Comparative Example G) and 80 days (Comparative Example H) after the preparation and storage of the aqueous dispersion at ambient temperature, the apparent viscosity of the aqueous dispersion was measured as a function of temperature according to a temperature sweep experiment described further above. The results are illustrated in FIG. 1.

FIG. 1 illustrates that the dispersion of Comparative Example F, that had only been stored for 14 days, displayed a large viscosity increase when the dispersion was heated to more than 32° C. in the temperature sweep experiment. This viscosity increase is advantageous when preparing capsule shells by dipping heated pins into the aqueous dispersion. The increased viscosity enables improved adhesion of the dispersion to the capsules.

However, it was observed that after storing the dispersion at ambient temperature over an extended time period, specifically for 27 days in Comparative Example G and 80 days in Comparative Example H, the observed viscosity increase already occurred when heating the dispersion to 30° C. in Comparative Example G or to 25° C. in Comparative Example H, respectively. This high viscosity increase close to room temperature requires cooling of the dispersion in some end-uses, for example in spraying operations, which adds complexity and increases energy costs.

Comparative Examples I-K and Examples 1 and 2

An aqueous HPCMAS dispersion was prepared as in Comparative Examples A-E except that sodium stearate as listed in Table 1 was used as a surfactant and that a Drais DCP-12 Advantis media mill (1.18 mm Ytterum Stabilized Zirconia media, 0.75 mm screen size) was used. The mill speed was initially set at 1100 rpm and then reduced as necessary down to about 750 rpm to control the mill outlet temperature.

In Comparative Example I the dispersion was not subjected to heat treatment during or after grinding. The apparent viscosity of the aqueous dispersion was measured 16 days after preparation after its production.

In Comparative Examples J and K and in Examples 1 and 2 the dispersion was stored at ambient temperature for more than 75 days after its preparation. Samples of the dispersion were subsequently heated to and kept at the temperature listed in Table 1 below for 3 hours. The temperatures during the heating period of 3 hours in Comparative Examples J and K and in Examples 1 and 2, respectively, were 30° C., 35° C., 40° C. and 50° C. After the heat treatment, on the same day, the apparent viscosity of the aqueous dispersion was measured as a function of temperature according to a temperature sweep experiment described further above. The results are illustrated in FIG. 2.

Figure 2:
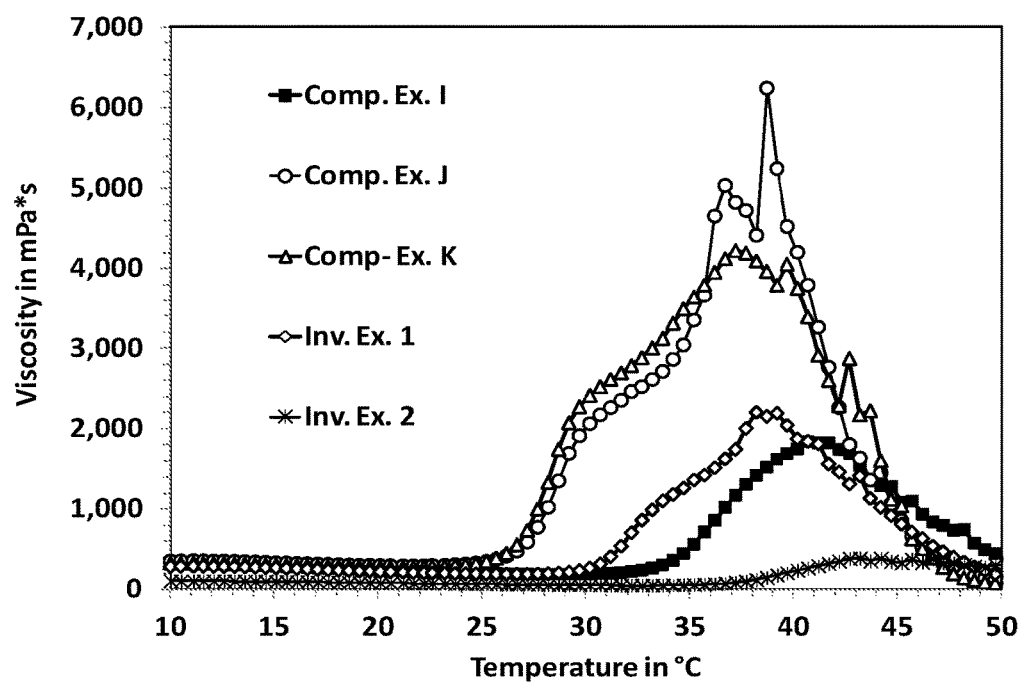
FIG. 2 illustrates the apparent viscosity of another aqueous dispersion of esterified cellulose ether particles produced according to a comparative process and according to the process of the present invention.

FIG. 2 illustrates that the dispersion of Comparative Example I 16 days after preparation displayed a significant viscosity increase when the dispersion was heated to more 34° C. in the temperature sweep experiment. This viscosity increase is advantageous when preparing capsule shells by dipping heated pins into the aqueous dispersion. However, for the dispersions of Comparative Examples J and K, which had been stored for more than 75 days before the measurement of the apparent viscosity, this viscosity increase already occurred at about 27° C. Heat treatment for 3 h at 30° C. or 35° C., respectively, was not sufficient to stabilize the dispersion against aging. In contrast thereto, in Example 1 the viscosity increase only occurred at about 32° C. Hence the heat treatment in Example 1 had the effect that the dispersion that had been stored for more than 75 days showed a similar behavior as a dispersion of Comparative Example I that had only been stored for 16 days. Heating the composition to a higher temperature during grinding as in Example 2 had the effect of reducing the viscosity increase of the produced dispersion at elevated temperatures. This is particularly desirable for coating applications.

Comparative Examples I K are not within the scope of the invention but do not represent prior art.

Examples 3-8

Examples 3-5: To produce an aqueous HPMCAS dispersion, HPMCAS, surfactant and optionally co-surfactant were added to water recirculating through a Drais DCP-12 Advantis media mill (1.0 mm ceramic media, 0.5 mm screen size). The mill speed was initially set at 1400-1500 rpm and then reduced as necessary down to about 1100-1400 rpm to control the mill outlet temperature.

HPMCAS and surfactant were pre-blended at a weight ratio to provide a percentage of surfactant based on HPMCAS, as listed in Table 1 below. The pre-blend of HPMCAS and surfactant was loaded in portions to water recirculating through the mill. Co-surfactant was loaded in portions throughout to provide a percentage of co-surfactant based on HPMCAS as listed in Table 1 below. The co-surfactant Aerosil OT 75 PG used in Examples 4 and 5 was a 75 wt. % solution of dioctyl sodium sulfosuccinate in propylene glycol and water comprising 0.12 wt. carboxymethyl cellulose. Aerosil OT 75 PG is commercially available from Cytec Industries Inc. The weight percent co-surfactant, based on HPMCAS, as listed in Table 1 below refers to the total weight of Aerosil OT 75 PG.

Addition continued until a total solids loading of 30-40% was achieved, based on the total weight of the composition. The percentage of HPMCAS, based on the total weight of the composition, was calculated from the measured solids content and the given weight ratio between HPMCAS, the surfactant and the optional co-surfactant. Following the addition of all solids, milling continued until the final particle size was obtained. The milling time was about 3 hours in Example 3, about 3.5 hours in Example 4 and about 5 hours in Example 5. During the milling process, mild heat treatment was applied by adjusting the mill speed and the setpoint for the chiller system used to provide cooling to the mill jacket, tank and heat exchangers. The maximum temperature during milling was 39-41° C.

Example 6

To produce an aqueous HPMCAS dispersion, the same mill as in Examples 3-5 was used. The mill speed was initially set at 1300-1400 rpm and then reduced as necessary down to about 1100 rpm to control the mill outlet temperature.

HPMCAS and surfactant were pre-blended at a weight ratio to provide percentage of surfactant, based on HPMCAS, as listed in Table 1 below. The pre-blend of HPMCAS and surfactant was loaded in portions to water recirculating through the mill. Co-surfactant was loaded in portions throughout to provide a percentage of co-surfactant based on HPMCAS as listed in Table 1 below. The co-surfactant "DSS 50%" as listed in Table 1 below was a 50 wt. % solution of dioctyl sodium sulfosuccinate in polyethylene glycol 400, NF. The weight percent co-surfactant, based on HPMCAS, as listed in Table 1 below refers to the total weight of the 50% dioctyl sodium sulfosuccinate solution. Addition continued and mild heat treatment was applied during the subsequent milling as described in Examples 3-5. The temperature during milling was most of the time from 30 to 40° C., but during about 50 min. the temperature was more than 40° C., the maximum being about 46° C. The total milling time was about 2 hours.

Example 7

Example 6 was repeated except that the temperature during milling was 43-47° C. for 2¾ hours, for the remaining time the milling temperature was 35-40° C. The total milling time was about 4.25 h.

Example 8

Example 6 was repeated except that the temperature during milling was 43-47° C. for about 4 hours. The total milling time was about 4.25 hours.

The dispersions of Examples 3-6 that had undergone a mild heat treatment in the mill could be stored for more than 3 months without losing their ability to flow under their own weight. The dispersions of Examples 7 and 8 that had undergone heat treatment for an extended time period in the mill could even be stored for more than 6 months without losing their ability to flow under their own weight.

Examples 5 and 8 illustrate that stable dispersions can be produced even at a very high HPMCAS concentrations of about 40 wt. % without unduly high viscosity of the dispersions at 20° C.

It was also found that in the dispersions of Examples 4-8, which all additionally comprised an anionic surfactant comprising a sulfate or sulfonate group, improved de-aeration was achieved, as compared to Example 3 which did not comprise a co-surfactant. Less air bubbles were formed in the dispersions of Examples 4-8 and/or formed air bubbles could be more easily removed from these dispersions.

Example 9a-9h

To produce an aqueous HPMCAS dispersion, the same mill as in Comparative Examples I-K and Examples 1 and 2 were used. The mill speed was initially set at 1200-1300 rpm and then reduced as necessary down to about 735 rpm to control the mill outlet temperature.

Figure 3:
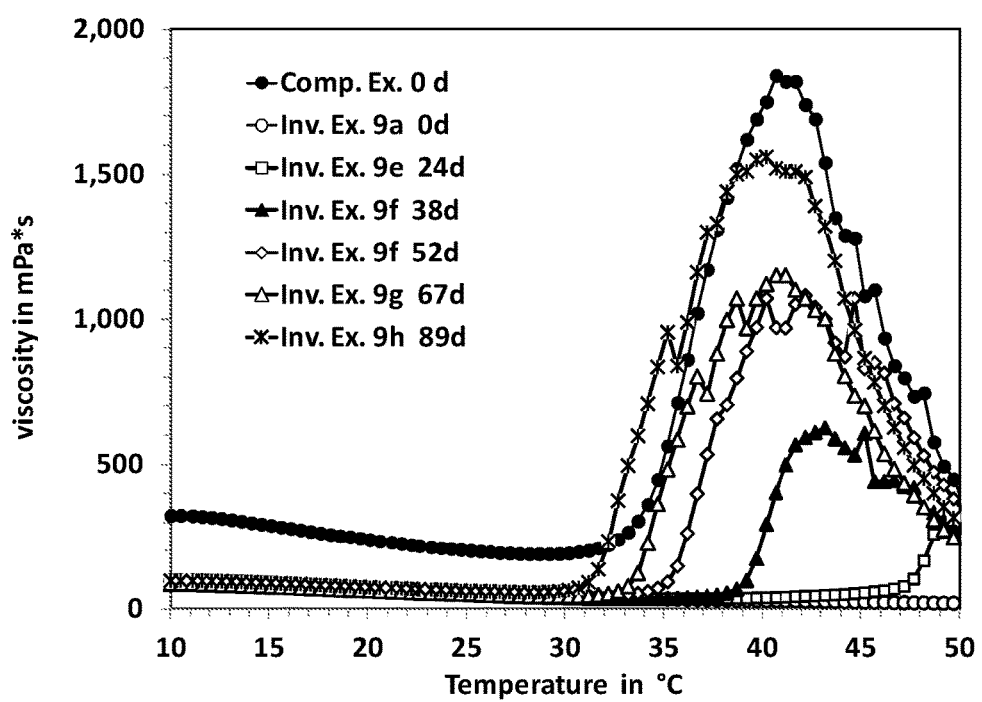
FIG. 3 illustrates the apparent viscosity of yet another aqueous dispersion of esterified cellulose ether particles produced according to a comparative process and according to the process of the present invention.

In Example 9a-h, the temperature during milling was less than 37° C. for 3.5 hours. Subsequently the dispersion was left standing in an oven at 45° C. for 16 hours. The apparent viscosity of the aqueous dispersion, produced according to the process of the present invention as described above, was measured as a function of temperature according to a temperature sweep experiment described further above. The first viscosity measurement was made 17 days after production. This was the start of a series of viscosity measurements after different storage periods. The viscosity was measured after the dispersion had been stored for the following number of days after production: 17+0 days (0 d), 17+3 days (3 d), 17+10 days (10 d), 17+24 days (24 d), 17+38 days (38 d), 17+52 days (52 d), 17+67 days (67 d) and 17+89 days (89 d) at ambient temperature, respectively. The results are illustrated in FIG. 3. The results for the storage for 17+3 days (3 d) and 17+10 days (10 d) were essentially the same as those for the storage at 17+0 days (0 d). To improve the legibility of FIG. 3, the results for the storage for 17+3 days (3 d) and 17+10 days (10 d) are not shown in FIG. 3.

Examples 9a-9h illustrate that the large viscosity increase of the dispersion at increased temperature is shifted to lower temperatures the longer the dispersion is stored. However, even after storage for 17+89 days (89 d), the viscosity increase only occurs at 32° C. or more. The dispersion of Example 9g, that had been produced according to the process of the present invention and subsequently stored for 17+67 days (67 d), and the dispersion of Comparative Example I, that had been stored for 16 days, both showed an large viscosity increase at about 34° C. Hence, due to the process of the present invention, the dispersion can be stored over 2 months longer while achieving a similar viscosity/temperature pattern as a comparative dispersion that has not been subjected to the heat treatment of the present invention.

Comparative Examples La and Lb

An aqueous HPCMAS dispersion was prepared as in Examples 3-5. The mill speed was initially set at 1300 rpm and then reduced as necessary down to about 800 rpm to control the mill outlet temperature. The temperature during milling was less than 37° C. for 4.5 hours. The dispersion was not put in an oven after milling In Comparative Example La the dispersion was not subjected to heat treatment during or after grinding. The apparent viscosity of the aqueous dispersion was measured 18 days after its production as a function of temperature according to a temperature sweep experiment described further above. The produced dispersion of Comparative Example La displayed a large viscosity increase when the dispersion was heated to more than 35° C. in the temperature sweep experiment. The viscosity increased from less than 500 mPa*s at 35° C. to above 2000 mPa*s at 40° C.

In Comparative Example Lb the film forming aid triethyl citrate (TEC) at an amount of 10 percent, based on the weight of HPMCAS, was added to dispersion of Comparative Example La. The apparent viscosity of the aqueous dispersion was measured one day after the addition of TEC. The dispersion of Comparative Example Lb already showed a large viscosity increase when the dispersion was heated to more than 27° C. in the temperature sweep experiment. The viscosity increased from about 500 mPa*s at 27° C. to above 2000 mPa*s at 30° C.

Comparative Examples La and Lb illustrate that the addition of a film forming aid such as TEC reduces the temperature at which the viscosity of the aqueous dispersion is increased to a large extent when the dispersion is heated in the temperature sweep experiment described further above.

Example 10a-10c

In Example 10a the apparent viscosity of the aqueous dispersion, produced according to the process of Example 9a, was measured as a function of temperature according to a temperature sweep experiment described further above. Example 10a corresponds to Example 9a. The viscosity of the 17 days old dispersion was below 200 mPa*s over the entire temperature range of 10 to 50° C.

In Examples 10b and 10c, respectively, the film forming aid triethyl citrate (TEC) at an amount of 10 percent and 21 percent, respectively, based on the weight of HPMCAS, was added to dispersion of Example 9a. The apparent viscosity of the aqueous dispersion was measured 1 day after the addition of TEC. The viscosity of the dispersions of Examples 10b and 10c was below 200 mPa*s over the entire temperature range of 10 to 50° C.

Examples 10a-10c illustrate that dispersions which have been produced according to the process of the present invention have a reasonably low temperature even at elevated temperatures and even upon addition of a film forming aid. This low viscosity is achieved in spite of a very high concentration of dispersed HPMCAS particles. Hence, the dispersions produced according to the process of the present invention have excellent utility for coating substrates, such as tablets and coatings. A high concentration of HPMCAS is highly desirable to increase the efficiency of preparing coatings. A low amount of aqueous diluent has to be evaporated. Moreover, a reasonably low viscosity of a broad temperature range facilitates the application of the dispersion, e.g. by spraying. Blocking of the spray nozzles can be minimized or even avoided, even when dispersion comprises a film forming agent. Applying the film forming agent through a separate spray nozzle is not necessary.

TABLE 1

| (Comparative) Example | Wt. % HPMCAS, based on total [%] | Wt. % Surfactant, based on HPMCAS | Wt. % Co-surfactant, based on HPMCAS | heat treatment (temp., time) | Mean* (µm) | d50* (µm) | d90* (µm) | Viscosity at 20° C. [mPa * s] | Stability after about 2 weeks | Mean after 2 weeks (µm) | Visual storage stability |
|---|---|---|---|---|---|---|---|---|---|---|---|
| A | 20.4 | — | — | — | 3.6 | 3.2 | 6.7 | 4970 | Aggl. | 44.8 | <1 week |
| B | 20.0 | 5.6% Tween 80 | — | — | 32.4 | 4.5 | 108.1 | 3120 | Aggl. | 91.5 | <1 week |
| C[1)] | | 4.8% SDS | — | — | NA | NA | NA | NA | NA | NA | <1 week |
| D | 24.2 | 0.7% SDS | — | — | 1.9 | 1.4 | 3.9 | 98 | Aggl. | 6.5 | <1 week |
| E | 20.8 | 4.8% Pluronic L-44 | — | — | 1.9 | 1.4 | 3.9 | 2830 | Increased part. size | 57.9 | <1 week |
| F-H | 30.2 | 4.8% Sodium Stearate | — | — | 2.5 | 2.0 | 5.4 | <600 | No Aggl. | NA | 2-3 months |
| I | 29.6 | 4.8% Sodium stearate | — | — | 2.3 | 1.8 | 4.9 | 239 | No Aggl. | 4.2 | 2-3 months |
| J | 29.6 | 4.8% Sodium stearate | — | 3 h at 30° C. | 2.9 | 1.9 | 5.9 | 297 | No Aggl. | NA | 2-3 months |
| K | 29.6 | 4.8% Sodium stearate | — | 3 h at 35° C. | 2.5 | 1.9 | 5.4 | 275 | No Aggl. | NA | 2-3 months |
| 1 | 29.6 | 4.8% Sodium stearate | — | 3 h at 40° C. | 4.1 | 2.1 | 7.6 | 83 | No Aggl. | NA | >6 months |
| 2 | 29.6 | 4.8% Sodium stearate | — | 3 h at 50° C. | 2.1 | 1.4 | 4.1 | 221 | No Aggl. | NA | >6 months |

TABLE 1-continued

| (Comparative) Example | Wt. % HPMCAS, based on total [%] | Wt. % Surfactant, based on HPMCAS | Wt. % Co-surfactant, based on HPMCAS | heat treatment (temp., time) | Mean* (μm) | d50* (μm) | d90* (μm) | Viscosity at 20° C. [mPa * s] | Stability after about 2 weeks | Mean after 2 weeks (μm) | Visual storage stability |
|---|---|---|---|---|---|---|---|---|---|---|---|
| 3 | 28.5 | 4.8% Sodium Stearate | — | at least 30 min >37° C. | 1.7 | 1.2 | 3.7 | 239 | No Aggl. | NA | >3 months |
| 4 | 35.7 | 3.0% Sodium Stearate | 1.0% Aerosil OT 75 | at least 30 min >37° C. | 2.4 | 2.0 | 4.9 | 1040 | No Aggl. | 2.5 | >3 months |
| 5 | 39.5 | 3.0% Potassium Stearate | 0.07% Aerosil OT 75 | at least 30 min >37° C. | 3.0 | 2.6 | 5.5 | 149 | No Aggl. | 3.2 | >3 months |
| 6 | 28.3 | 3.0% Sodium Stearate | 1.0% DSS 50% | 50 min at >40° C. | 2.4 | 1.9 | 4.8 | 546 | No Aggl. | 2.8 | >3 months |
| 7 | 28.6 | 4.0% Sodium Stearate | 1.0% DSS 50% | 2½ hours at >40° C. | 2.4 | 1.9 | 4.9 | 196 | No Aggl. | 2.4 | >6 months |
| 8 | 38.1 | 4.0% Sodium Stearate | 1.0% DSS 50% | 4 hours at >40° C. | 2.2 | 2.1 | 4.1 | 2280 | No Aggl. | 2.9 | >6 months |
| 9a-9h and 10a-10c | 29.9 | 4.8% Sodium stearate | — | 16 hours at 45° C. | 2.2 | 1.7 | 4.7 | <500 | No Aggl. | NA | >3 months |
| La/Lb | 29.9 | 4.8% Sodium stearate | — | — | 2.0 | 1.4 | 4.6 | <500 | No Aggl. | 2.4 | 2-3 months |

NA: not assessed
Aggl: Agglomeration
No Aggl: No Agglomeration
[1] viscosity too high, the mill was inoperable
*Particle size distribution of the freshly prepared dispersion

The invention claimed is:

1. A process for producing an aqueous composition comprising a dispersed esterified cellulose ether comprising the steps of
grinding, in the presence of an aqueous diluent, at least one esterified cellulose ether comprising (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation,
blending at least one salt of a fatty acid and optionally one or more adjuvants with the esterified cellulose ether before, during or after the grinding of the esterified cellulose ether and choosing the amounts of aqueous diluent, esterified cellulose ether, salt of a fatty acid, and optionally one or more adjuvants that the produced aqueous composition comprises at least 25 percent of the dispersed esterified cellulose ether, based on the total weight of the aqueous composition, and
heating the aqueous composition to a temperature of from 37 to 80° C. during or after the grinding step.

2. The process of claim 1 wherein additionally an anionic surfactant comprising a sulfate or sulfonate group is blended with the esterified cellulose ether before, during or after the grinding of the esterified cellulose ether.

3. The process of claim 1 wherein the aqueous composition is heated to a temperature of from 40 to 70° C.

4. The process of claim 3 wherein the aqueous composition is heated to a temperature of from 40 to 55° C.

5. The process of claim 1, wherein the aqueous composition is heated during a time period of at least 30 minutes.

6. The process of claim 1, wherein the median particle size, d50, of the dispersed esterified cellulose ether particles is up to 7 micrometers, the median particle size, d50, being the size at which 50 volume percent of the particles have a smaller equivalent diameter and 50 volume percent have a larger equivalent diameter.

7. The process of claim 1 wherein the aqueous composition comprises at least 30 weight percent of said at least one dispersed esterified cellulose ether, based on the total weight of the aqueous composition.

8. The process of claim 1 wherein the aliphatic monovalent acyl groups in the esterified cellulose ether are acetyl, propionyl or butyryl groups, and the groups of the formula —C(O)—R—COOA are —C(O)—CH2-CH2-COOA, —C(O)—CH=CH—COOA, or —C(O)—C6H4-COOA groups.

9. The process of claim 1 wherein the esterified cellulose ether is hydroxypropyl methyl cellulose acetate succinate.

10. The process of claim 1 wherein the amount of the salt of a fatty acid is from 0.05 to 20 percent, based on the weight of the esterified cellulose ether.

11. The process of claim 1 wherein the salt of a fatty acid is an alkali metal or alkaline earth metal salt of stearic acid.

12. The process of claim 1 wherein the anionic surfactant comprising a sulfate or sulfonate group is a dialkyl sulfosuccinate.

13. The process of claim 1 wherein a film forming aid is added to the aqueous composition after heating the aqueous composition to a temperature of from 37 to 80° C.

* * * * *